(12) United States Patent
Wilson et al.

(10) Patent No.: US 7,650,733 B2
(45) Date of Patent: Jan. 26, 2010

(54) METHOD AND APPARATUS FOR LOADING A CONTAINER WITH A PRODUCT

(75) Inventors: Alan Anthony Wilson, Ware (GB); Phillip William Farr, Ware (GB); Marcus Edward Pike, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/235,319

(22) Filed: Sep. 22, 2008

(65) Prior Publication Data

US 2009/0013652 A1    Jan. 15, 2009

Related U.S. Application Data

(63) Continuation of application No. 09/979,569, filed as application No. PCT/EP00/04499 on May 18, 2000, now Pat. No. 7,426,815.

(30) Foreign Application Priority Data

May 21, 1999    (GB)    ................................. 9911770.7

(51) Int. Cl.
    *B65B 37/20*    (2006.01)
(52) U.S. Cl. ............................. 53/560; 53/527; 53/272; 53/454
(58) Field of Classification Search ................... 53/359, 53/341, 266.1, 267, 272, 274, 900, 436, 454, 53/560, 527
    See application file for complete search history.

(56) References Cited

U.S. PATENT DOCUMENTS

| 2,365,920 | A | 12/1944 | Vaughn |
| 3,315,713 | A | 4/1967 | Kincaide |
| 3,554,412 | A | 1/1971 | Hayashi |
| 3,565,132 | A | 2/1971 | Lefort |
| 3,656,518 | A | 4/1972 | Aronson |
| 3,718,164 | A | 2/1973 | Stewart |
| 4,182,383 | A | 1/1980 | Adomitis et al. |
| 4,314,653 | A | 2/1982 | Sindoni |
| 4,469,144 | A | 9/1984 | Burns |
| 4,481,987 | A | 11/1984 | Burns |
| 4,542,835 | A | 9/1985 | Gamberini |
| 4,607,479 | A | 8/1986 | Linden |
| 4,628,971 | A | 12/1986 | Belot |
| 4,688,610 | A | 8/1987 | Campbell |
| 4,731,979 | A | 3/1988 | Yamamoto et al. |
| 4,850,259 | A | 7/1989 | Morris |
| 5,082,032 | A | 1/1992 | Crocker |
| 5,111,642 | A | 5/1992 | Chiari |
| 5,143,126 | A | 9/1992 | Boesch et al. |
| 5,145,009 | A | 9/1992 | Mheidle et al. |

(Continued)

FOREIGN PATENT DOCUMENTS

DE    2346070 A1    3/1975

(Continued)

*Primary Examiner*—Christopher Harmon
(74) *Attorney, Agent, or Firm*—Dwight S. Walker

(57) ABSTRACT

There is provided a method of loading a container with a defined quantity of product which comprises the steps of a) closing off a perforation (12a, 12b) in a perforated plate (10); b) directing powder (30) into said closed-off perforation; and c) transferring the contents of the perforation to said container.

15 Claims, 7 Drawing Sheets

U.S. PATENT DOCUMENTS

| | | | |
|---|---|---|---|
| 5,192,548 A | 3/1993 | Valesquez et al. |
| 5,240,049 A | 8/1993 | Chiari |
| 5,287,897 A | 2/1994 | Gamberini |
| 5,320,146 A | 6/1994 | Stevie |
| 5,549,144 A | 8/1996 | Dworak et al. |
| 5,662,849 A | 9/1997 | Bogue et al. |
| 5,855,233 A | 1/1999 | Bolelli |
| 5,934,343 A | 8/1999 | Gaylo et al. |
| 5,950,868 A | 9/1999 | Wegman |
| 6,035,905 A | 3/2000 | Griffin |
| 6,098,675 A | 8/2000 | Runft |
| 7,426,815 B1 | 9/2008 | Wilson et al. |
| 2005/0118260 A1 | 6/2005 | Bailey et al. |

FOREIGN PATENT DOCUMENTS

| | | |
|---|---|---|
| DE | 3607187 A1 | 9/1987 |
| DE | 3618041 A1 | 12/1987 |
| DE | 19533233 A1 | 3/1997 |
| DE | 19651237 A1 | 6/1998 |
| EP | 0282958 A1 | 9/1988 |
| EP | 0768122 A2 | 4/1997 |
| EP | 0823324 A1 | 2/1998 |
| EP | 0903290 A1 | 3/1999 |
| FR | 2419235 | 10/1979 |
| GB | 353594 | 7/1931 |
| GB | 2167387 A | 5/1986 |
| JP | 541280 A | 1/1979 |
| JP | 62146102 A | 6/1987 |
| JP | 336393 U | 4/1991 |
| JP | 726074 U | 5/1995 |
| JP | 5324387 U | 1/2000 |
| NL | 8801521 | 1/1990 |
| SU | 690314 A | 10/1979 |
| SU | 1027081 A | 7/1983 |
| SU | 1062149 A | 12/1983 |
| SU | 1105761 A | 7/1984 |
| SU | 1285440 A | 1/1987 |
| SU | 1357718 A | 12/1987 |
| SU | 1488143 A | 6/1989 |
| WO | 9521768 A1 | 8/1995 |
| WO | 9531239 A1 | 11/1995 |
| WO | 9617776 A1 | 6/1996 |
| WO | 9635565 A1 | 11/1996 |
| WO | 9711884 A1 | 4/1997 |
| WO | 9718991 A1 | 5/1997 |
| WO | 9741031 A1 | 11/1997 |
| WO | 9741821 A1 | 11/1997 |
| WO | 9919215 A1 | 4/1999 |
| WO | 0007881 | 2/2000 |
| WO | 0032474 A1 | 6/2000 |
| WO | 0071419 A1 | 11/2000 |
| WO | 0071424 A1 | 11/2000 |

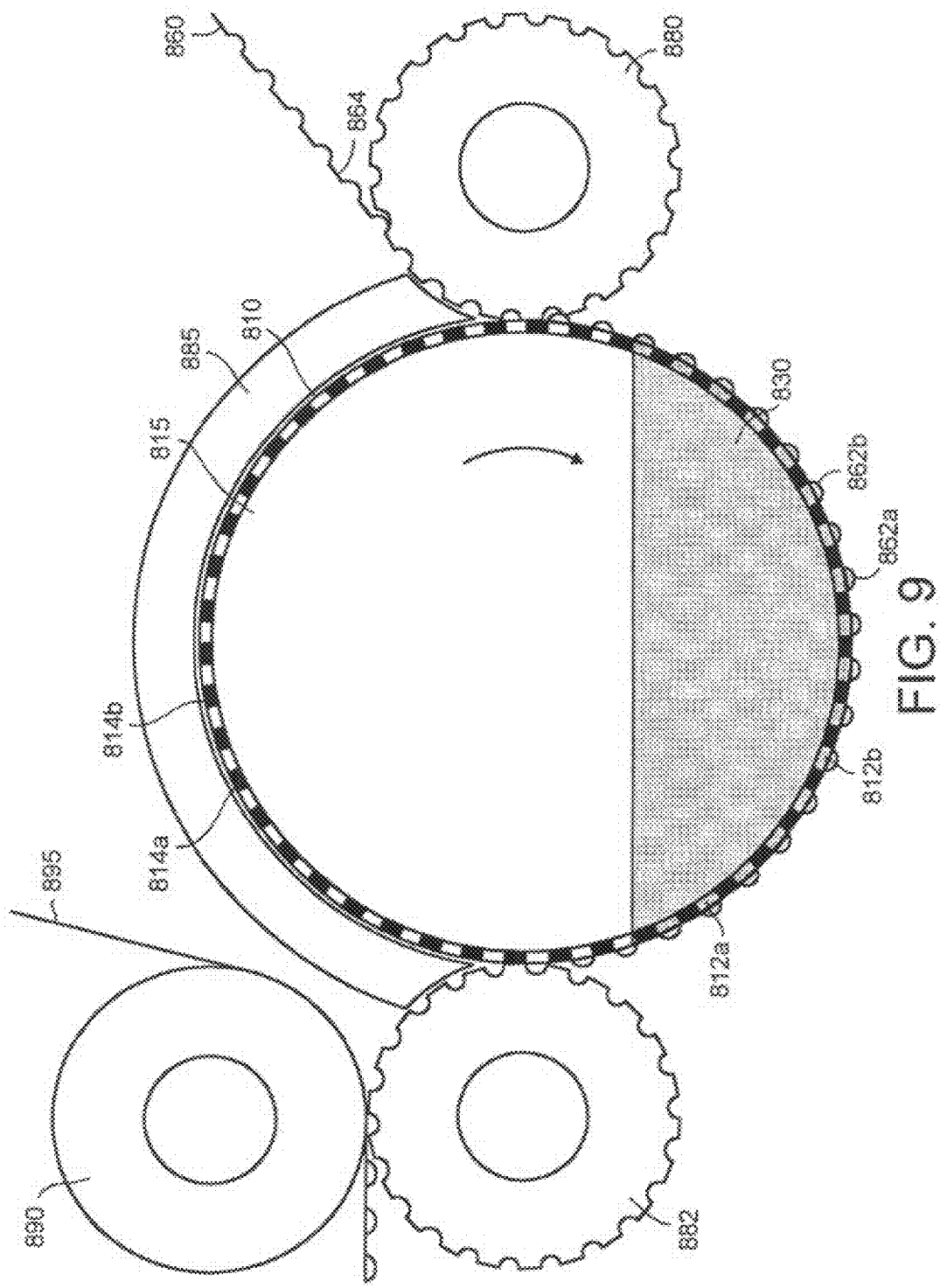

METHOD AND APPARATUS FOR LOADING A CONTAINER WITH A PRODUCT

CROSS-REFERENCE TO RELATED APPLICATIONS

This application is a Continuation of U.S. patent application Ser. No. 09/979,569 filed 19 Nov. 2001, now U.S. Pat. No. 7,426,815 issued 23 Sep. 2008; which was a US National Phase Application filed under the Patent Cooperation Treaty of International Patent Application No. PCT/EP00/04499 filed 18 May 2000; which claims priority from GB 9911770.7 filed 21 May 1999 in the United Kingdom.

FIELD OF INVENTION

This invention relates to a method and apparatus for loading a container with a defined quantity of product. This invention has particular application to loading a blister in a blister pack with a defined quantity of medicament.

BACKGROUND TO THE INVENTION

The use of blister packs to hold medicaments for inhalation devices, for example in bronchodilation therapy, is well known. The blister packs usually consist of a base sheet in which blisters are formed. The blisters are arranged on the base sheet and can be filled with medicament to be administered through use of an inhalation device. A lid sheet is applied to cover the filled blisters and the two sheets are sealed together to form a blister pack.

There can, however, be problems associated with methods of filling the blisters with medicament. Powder, particularly the drug component of the powder, can tend to be attracted to the base sheet surface rather than to the blister pockets. This attraction of the drug to the base sheet can result in inaccurate filling of the blisters, create mess and potentially cause problems with adherence of the lid sheet to the base sheet. Such filling methods may also require a large reservoir of powder, potentially resulting in waste of the medicament.

The Applicants have now found that the potential problem of powder adherence can be overcome by using a filling method utilising a perforated plate to mask the base sheet surface during filling to avoid covering this area with powder. The perforated plate is simply moved into contact with the appropriate areas of the blister strip during filling and then moved away at the end of the method and can be reused in each cycle. This filling method, therefore, aims to prevent the powder adhering to the blister strip, rather than relying on using methods such as additional cleaning steps to remove the powder after it has accumulated. The filling method can also be used to fill other types of containers e.g. injection moulded plastic pockets, capsules or bulk containers.

The perforated plate is also used to assist with ensuring the correct dose of powder is loaded into the blind cavity. In one aspect, adjusting the size of the perforation enables different doses to be loaded into the blisters.

Another problem associated with filling blister packs with powdered medicament is that the powder often has poor flow properties, making accurate filling difficult. The applicants have found that this problem can be overcome by the use of a director, for example a blade, which can direct the powder into the perforations. The blade can be passed through the powder several times or multiple blades may be used to ensure that filling is accurate.

The applicants have also found that the method and apparatus described herein can also be used to form tablets by applying increased compaction forces to the powder. The use of this method avoids many of the pre-processing steps (e.g. granulation) usually involved in tablet formation by gravity feed of the powder.

SUMMARY OF THE INVENTION

According to the present invention there is provided a method of loading a container with a defined quantity of product which comprises:

a) closing off a perforation in a perforated plate;
b) directing powder into said closed-off perforation; and
c) transferring the contents of the perforation to said container.

Preferably, the closing off is achievable by the use of a blanking plate.

Alternatively, the closing off is achievable by the use of a blanking pin inserted into the perforation. Preferably the blanking pin is moveable within the perforation to adjust the volume of the closed-off perforation.

Alternatively, the closing off is achievable by placing a container in registration with the perforation.

Preferably, the diameter of the closed-off perforation is between 1.5 and 15 mm. The perforation may be a variety of shapes, such as square, circular, oval or rectangular.

Preferably, the powder is directable by the action of a first leveller blade movable relative to the perforated plate. Preferably said first leveller blade moves on a linear sweeping path. Prior art filling systems often use either rotary levelling blades or systems or a static blade in a rotating powder filled bowl. Linear movement of the leveller blade has several advantages over a rotary system. For example, linear movement of the powder across the powder bed by the leveller blade can produce a powder bed with a more uniform density than a rotary system. Linear movement of the powder is also more suited to a linear pack or strip and less powder may be required. There may also be less powder wastage than with a rotary system. The leveller blade may move either across the length or width of the perforated plate.

In one aspect, the first leveller blade is perpendicular to the linear sweeping path.

Alternatively, the first leveller blade presents a forward acute angle to the linear sweeping path. That is to say, the angle between the direction of the sweeping path and the blade is less than 90°. Preferably the forward acute angle is between 1 and 60°. More preferably the forward acute angle is between 5 and 25°.

Alternatively, the first leveller blade presents multiple forward acute angles to the linear sweeping path. Such a first leveller blade is typically articulated or curved.

It is also possible to use a first leveller blade presenting a forward obtuse angle to the linear path.

Optionally, the first leveller blade has plural movements relative to the perforated plate. The number of plural movements can be varied according to the flow properties of the powder to help ensure that the powder has a uniform density, resulting in more accurate dosing. Passing a leveller blade across the perforated plate more than once may in some circumstances be more economical than having multiple blades, although the time taken to fill the closed-off perforations may be greater than when using multiple blades.

Preferably, a thin layer of powder is left on the perforated plate after movement of the first leveller blade. Preferably the depth of said thin layer of powder is from 3 to 20 mm. More preferably the depth of said thin layer of powder is from 4 to 8 mm.

Preferably, the powder is directable by at least one subsequent leveller blade. Preferably, the at least one subsequent leveller blade moves along the perforated plate at a lower level than that of the first leveller blade. This ensures that the at least one subsequent leveller blade can move through the thin layer of powder left by the first leveller blade and not just along the surface of the powder.

Preferably, the distance between the level of movement of the first leveller blade and the at least one subsequent leveller blade is 0 to 12 mm. More preferably the distance between the level of movement of the first leveller blade and the at least one subsequent leveller blade is 1 to 3 mm. A second subsequent leveller blade would move along the perforated plate at a lower level to that of a first subsequent leveller blade.

According to one embodiment of the invention the perforated plate forms the rim of a drum. In one aspect, the powder is directable into the perforations of the perforated plate by gravity as the drum rotates.

An additional component of the invention comprises removing excess powder from said perforated plate subsequent to directing powder into the perforation. Preferably the excess powder is removed by the action of a wiper. The wiper is typically a blade composed of stainless steel and moves in close proximity to the surface of the perforated plate to ensure that excess powder is not transferred to the blind cavity.

Preferably, the contents of the perforation are transferable by the action of a transfer pin. The pin is inserted into the perforation, transferring the powder through to the blind cavity.

Preferably the direction of powder into the closed-off perforation and transfer into the blind cavity is a continuous step.

Alternatively, transfer of the contents of the perforation to the container comprises:

a) reopening the perforation;

b) placing the container in registration with the perforation; and c) transferring the contents of the perforation into the container.

Alternatively, the contents of the perforation are transferable by the action of a vacuum system. Preferably the vacuum comprises a vacuum head and at least one vacuum cup.

An additional component of the invention comprises compacting the powder in the perforation.

Preferably, the powder is compacted to a volume of between 70 and 100% of the original volume of powder in the closed-off perforation.

Alternatively, the powder is compacted to form a tablet.

Preferably, the powder is compactable by the action of a compacting pin. Preferably the transfer pin and the compacting pin are integral. More preferably the transfer pin and the compacting pin are identical.

Preferably, the container is a blind cavity. Preferably, the blind cavity is selected from the group consisting of a blister pocket, an injection moulded plastic pocket, a capsule and a bulk container. A blister pocket or injection moulded plastic pocket may form part of an elongate strip used in inhalation devices.

An additional component of the invention comprises applying a lid to the container to protect the contents therein. The lid may then be sealed to the container.

Preferably, the powder comprises a medicament. Preferably the medicament is selected from the group consisting of albuterol, salmeterol, fluticasone propionate and beclomethasone dipropionate and salts or solvates thereof and any mixtures thereof. A preferred combination comprises salmeterol xinafoate and fluticasone propionate. Optionally, excipient such as lactose or another sugar may be present together with the medicament.

The invention also provides an apparatus for loading a container with a defined quantity of product, which comprises:

a) a perforated plate;

b) a closure for reversibly closing off a perforation in the perforated plate;

c) a director for directing powder into said perforation; and d) a transferor for transferring the contents of the perforation to said container.

The perforated plate forms the basis for a powder reservoir and may have side walls to form a container suitable for holding powder.

Preferably, the closure comprises a blanking plate.

Preferably, the closure comprises a blanking pin inserted into the perforation. Preferably the blanking pin is moveable within the perforation to adjust the volume of the perforation.

Alternatively, the closure comprises the container placed in registration with the perforation.

Preferably, the diameter of the closed-off perforation is between 1.5 and 15 mm. The perforation may be a variety of shapes, such as square, circular, oval or rectangular.

Preferably, the director comprises a first leveller blade movable relative to the perforated plate. Preferably, said first leveller blade is movable across the perforated plate on a linear sweeping path. Preferably, the first leveller blade is positioned to leave a gap of between 3 and 20 mm between the first leveller blade and the perforated plate. More preferably the first leveller blade is positioned to leave a gap of between 4 and 8 mm between the first leveller blade and the perforated plate.

Preferably, the director comprises at least one subsequent leveller blade. Preferably, the at least one subsequent leveller blade is positioned closer to the perforated plate than the first leveller blade. Preferably, the at least one subsequent leveller blade is positioned 0 to 12 mm closer to the perforated plate than the first leveller blade. More preferably the at least one subsequent leveller blade is positioned 1 to 3 mm closer to the perforated plate than the first leveller blade. A second subsequent leveller blade would move along the perforated plate at a lower level to that of a first subsequent leveller blade.

According to an alternative embodiment of the invention the perforated plate forms the rim of a drum. In one aspect, the powder is directed into the perforations of the perforated plate by gravity as the drum rotates.

Preferably, the transferor comprises a transferor pin.

Alternatively, the transferor comprises a vacuum system. Preferably the vacuum system comprises a vacuum head and a series of vacuum cups.

An additional component of the invention comprises a compactor for compacting the powder in the perforation. Preferably, the compactor comprises a compactor pin.

Preferably, the transferor and compactor are integral. More preferably the transferor and compactor are identical.

An additional component of the invention comprises registration means for registering the container with the perforation.

An additional component of the invention comprises a powder remover for removing excess powder from the perforated plate subsequent to action of the powder director. Preferably, the powder remover comprises a wiper. The wiper is typically a blade composed of stainless steel and moves in close proximity to the surface of the perforated plate to ensure that excess powder is not transferred to the blind cavity.

Preferably, the container is a blind cavity. Preferably, the blind cavity is selected from the group consisting of a blister pocket, an injection moulded plastic pocket, a capsule and a bulk container. A blister pocket or injection moulded plastic pocket may form part of an elongate strip used in inhalation devices.

An additional component of the invention comprises a lid applier for applying a lid to the container to protect the powder therein.

Preferably, the apparatus further comprises powder. Preferably, the powder comprises a medicament. Preferably, the medicament is selected from the group consisting of albuterol, salmeterol, fluticasone propionate and beclomethasone dipropionate and salts or solvates thereof and any mixtures thereof. A preferred combination comprises salmeterol xinafoate and fluticasone propionate.

The invention also provides a tablet obtainable by the method as herein described. Alternatively the invention provides compacted powder obtainable by the method as herein described.

BRIEF DESCRIPTION OF THE DRAWINGS

The invention will now be described with reference to the accompanying drawings in which:

FIG. 8b shows an optional subsequent stage in the alternative filling method of FIG. 8a; and FIG. 9 shows a further alternative filling method in accord with the present invention.

DETAILED DESCRIPTION OF THE DRAWINGS

Figure 1A:
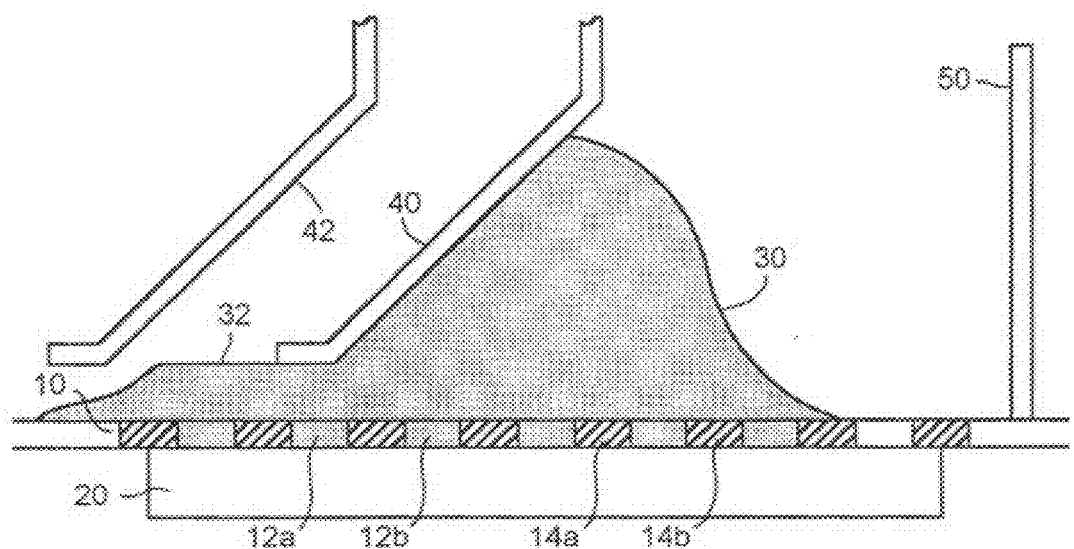
FIGS. 1a, 1b and 1c show the first stage in a filling method in accord with the present invention.
Figure 1B:
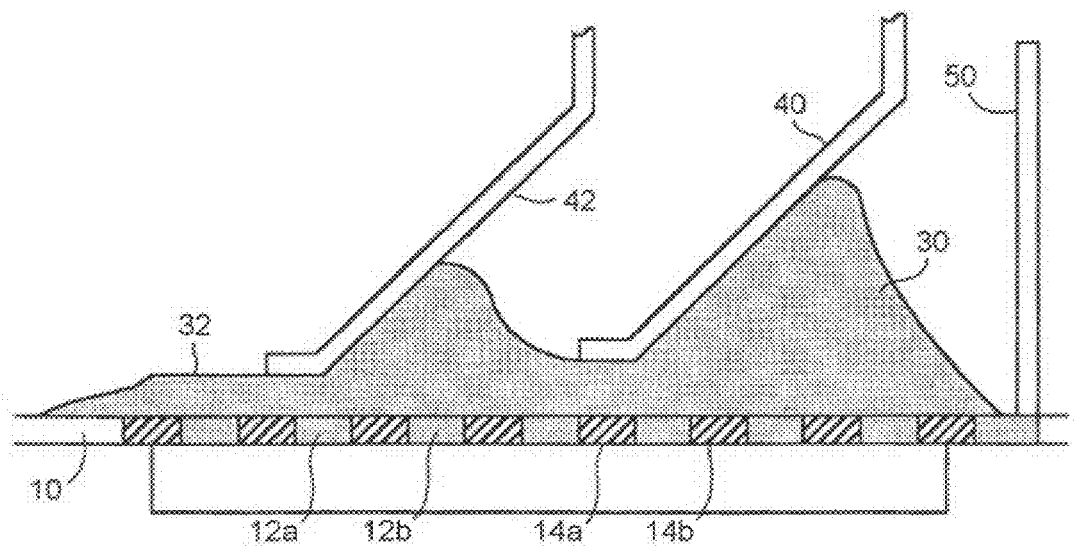
Figure 1C:
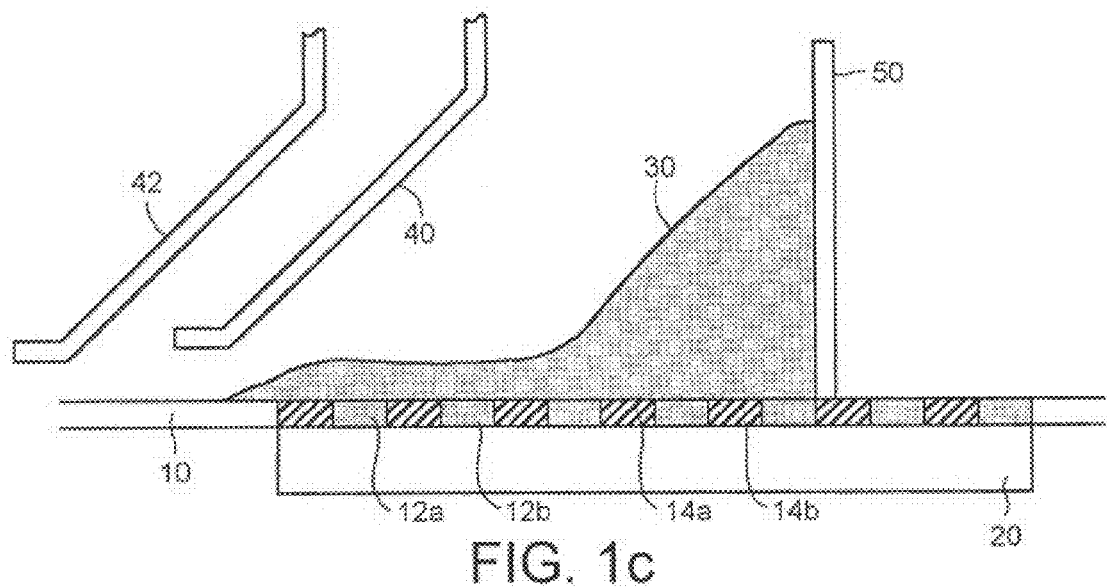

FIGS. 1a, 1b and 1c show the first stages in a filling method herein. A perforated plate 10 in contact with a blanking plate 20 creates closed-off perforations 12a, 12b. On the opposite side of the perforated plate 10 to the blanking plate 20 is a reservoir of powder 30. The powder 30 comprises a suitable medicament formulation. Situated above the powder reservoir are leveller blades 40, 42 and wiper blade 50. The leveller blades may be seen to have following tail sections.

The leveller blades 40, 42 are shown mounted at an angle of approximately 45° to the perforated plate 10. It should however be appreciated that the leveller blades 40, 42 may be mounted at any angle within a wide range, typically (but not exclusively) at an acute angle and preferably between 1 and 60°, and may be varied according to the properties of the powder to optimise powder direction. When the blades are angled at an acute angle they exert a compressive force on the powder which produces a powder bed with a more uniform density than using perpendicular blades. However, it is also possible to use blades that are perpendicular to the linear path or are mounted at an obtuse angle to the linear path. It should be appreciated that curved or articulated blades may alternatively be used. The tail sections of the leveller blades 40, 42 are not essential to their action although they may also be angled and exert a further compressive force on the powder. The wiper blade 50 is shown mounted at an angle of approximately 90° to the perforated plate 10, however effective operation of the wiper 50 can be obtained within a wide range of angles.

The powder 30 is directed into the perforations 12a, 12b by the action of leveller blades 40,42 which move across the powder reservoir 30 on a sweeping linear path, moving the powder 30 along the length or width of the perforated plate 10. The first leveller blade 40 moves through the powder reservoir 30 leaving a thin layer of excess powder 32 still in contact with the perforated plate 10. The second leveller blade 42 moves across the perforated plate 10 at a lower level than the first leveller blade 40, moving through the thin layer of excess powder 32 and directing powder 30 into any spaces in the perforations 12a, 12b not filled by the action of the first leveller blade 40. Additional leveller blades may follow the second leveller blade 42 if required. Alternatively, the leveller blades 40, 42 may be passed through the powder reservoir 30 more than once if the powder has poor flow properties. The leveller blades, 40, 42 may then be moved back across the powder reservoir 30, without disrupting the thin layer of excess powder 32, or alternatively turned around ready for travel in the opposite direction, so that they are ready for use in the next filling cycle. A wiper 50, typically a blade composed of stainless steel, then moves along the powder reservoir 30 in close proximity to the surface of the perforated plate 10, removing the excess powder 32 from the perforated plate surface 10.

Figure 2:
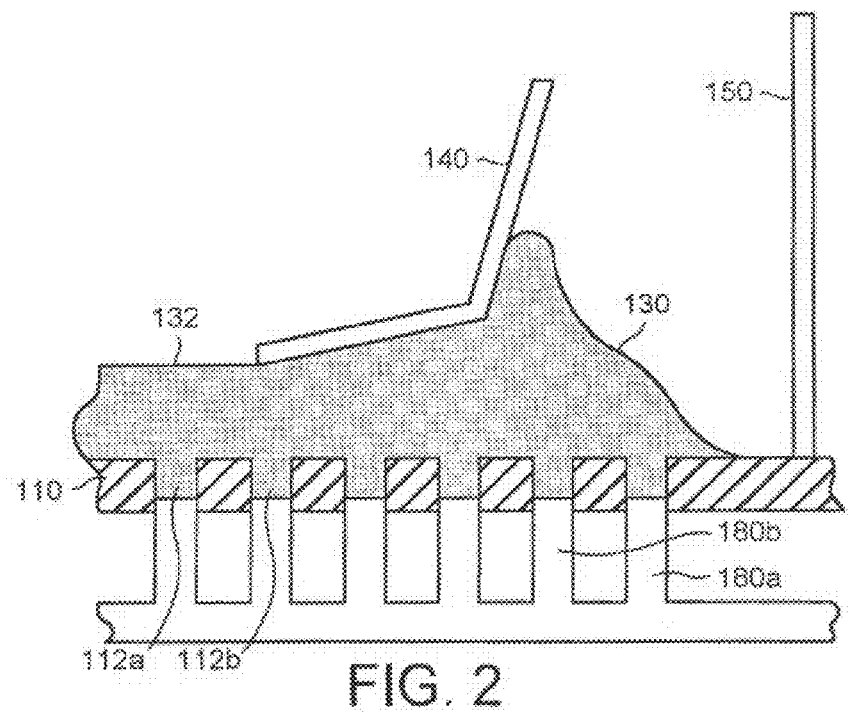
FIG. 2 shows the first stage in an alternative filling method in accord with the present invention.

FIG. 2 shows the first stage in an alternative filling method herein. Blanking pins 180a, 180b are inserted into a perforated plate 110 to create closed-off perforations 112a, 112b. The volume of the closed-off perforations 112a, 112b may be varied by varying the insertion depth of the blanking pins 180a, 180b. On the opposite side of the perforated plate 110 to the blanking pins 180a, 180b is a reservoir of powder 130. The powder 130 comprises a suitable medicament formulation. The powder 130 is directed into the perforations 112a, 112b (as shown in FIGS. 1a and 1b) by the action of a leveller blade 140 which moves across the powder reservoir 130 on a linear path and moves the powder 130 along the length of the perforated plate 110, leaving a thin layer of excess powder 132 still in contact with the perforated plate 110. The leveller blade shown illustrates a blade with a longer tail section than the blades shown in FIGS. 1a, 1b and 1c and this tail section is shown angled at about 10° to the linear path. However it should be appreciated that any blade in accord with the present invention may be used to fill the perforations closed off by the blanking pins. A wiper 150 follows the leveller blade 140 (as shown in FIG. 1c) and moves along the powder reservoir 130 in close proximity to the surface of the perforated plate 110, removing the excess powder 132 from the perforated plate surface 110.

Figure 3:
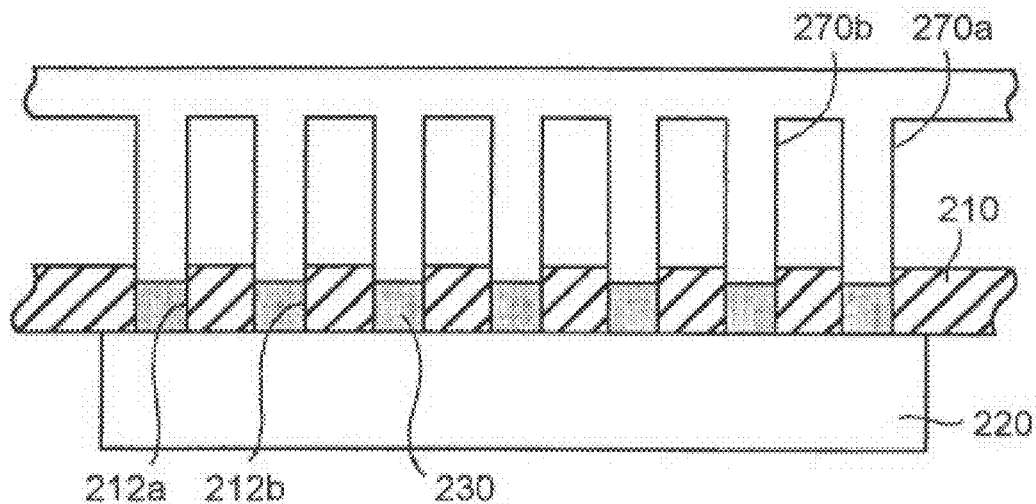
FIG. 3 shows an optional subsequent compaction stage in the filling method of FIGS. 1a, 1b, 1c and 2.

FIG. 3 shows an optional subsequent stage to FIGS. 1a, 1b 1c and FIG. 2 in which compaction pins 270a, 270b are inserted into the closed-off perforations 212a, 212b to compact the powder 230 held within the perforation 212a, 212b. The figure shows a blanking plate 220 acting to close off the perforations as in FIGS. 1a, 1b and 1c however it should be appreciated that this stage is also applicable to the situation where blanking pins are used to close off the perforations as in FIG. 2. The blanking plate 220 may then be removed from its position in contact with the perforated plate 210 or the blanking pins removed from the closed-off perforations 212a, 212b. The powder 230 generally has poor flow properties and therefore remains in the perforations 212a, 212b.

Figure 4:
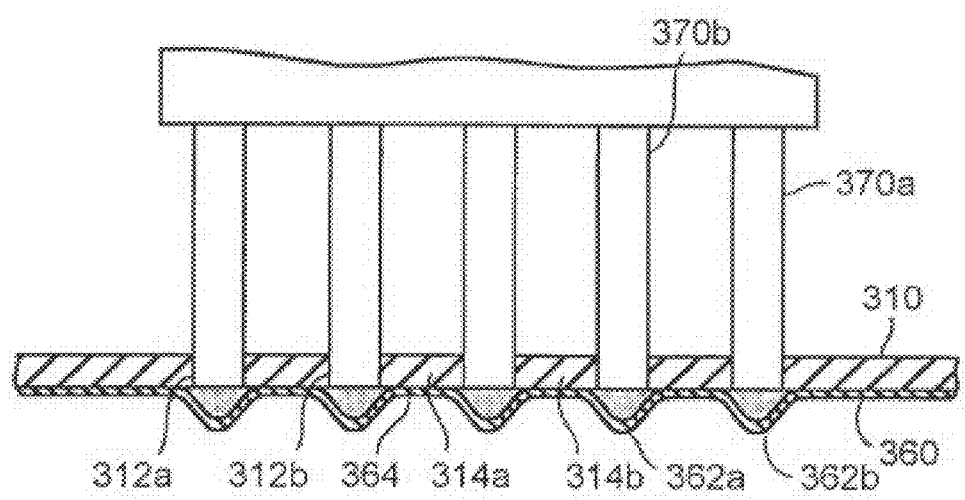
FIG. 4 shows a subsequent transfer stage in the filling method of FIGS. 1a, 1b, 1c and 2.

FIG. 4 shows a further stage to FIGS. 1a, 1b, 1c, 2 and 3 in which a blister strip 360 is moved so that it is positioned with blister pockets 362a, 362b in line with the perforations 312a, 312b. The solid sections 314a, 314b of the perforated plate 310 mask the surface surrounding the pockets 364. The transfer pins 370a, 370b are inserted through the perforated plate 310 and the powder 330 is transferred to the blister pockets 362a, 362b. The filled blister strip 360 is then lowered and the pins 370a, 370b raised. The blanking plate 320 is relocated against the underside of the perforated plate 310, creating closed-off perforations 312a, 312b, which are filled with powder 330 in the next cycle.

It should be appreciated that the powder can also be transferred to other types of container, for example an injection moulded container, a capsule or other form of blind cavity.

Figure 5:
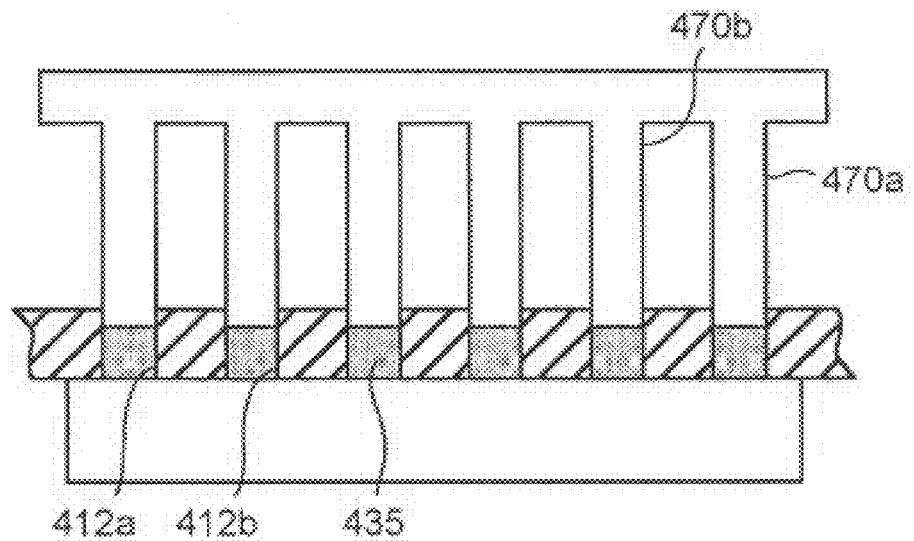
FIG. 5 shows an alternative subsequent stage to the compaction stage of FIG. 3 in the filling method of FIGS. 1a, 1b, 1c and 2.

FIG. 5 shows an alternative stage subsequent to FIGS. 1a, 1b, 1c and 2 in which the compaction pins 470a, 470b are inserted into the closed-off perforations 412a, 412b to compact the powder 430 held within the perforation 412a, 412b. The force applied to the powder 430 is sufficient to compress the powder 430 enough to form a tablet 435.

Figure 6:
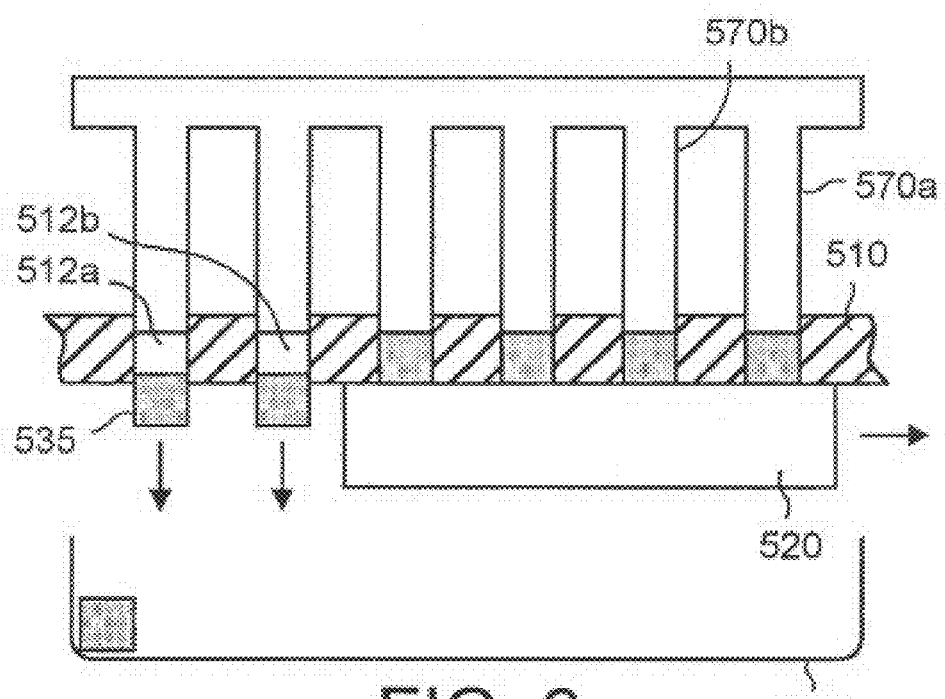
FIG. 6 shows a transfer stage subsequent to the subsequent stage of FIG. 5.

FIG. 6 shows a transfer stage subsequent to FIG. 5 in which the blanking plate 520 (or other blanking method e.g. blanking pins) is removed from its position in contact with the perforated plate 510, allowing the tablets 535 to fall out of the perforations and be collected by a bulk container 566. The transfer pins 570a, 570b may be used to help push the tablets 535 through the perforations 512a, 512b. The tablets may then be subjected to further processing steps before packaging. It should be appreciated that the tablets 535 may be transferred to other types of container such as a blister strip following an additional step to register the blister pockets with the perforations 512a, 512b.

Figure 7A:
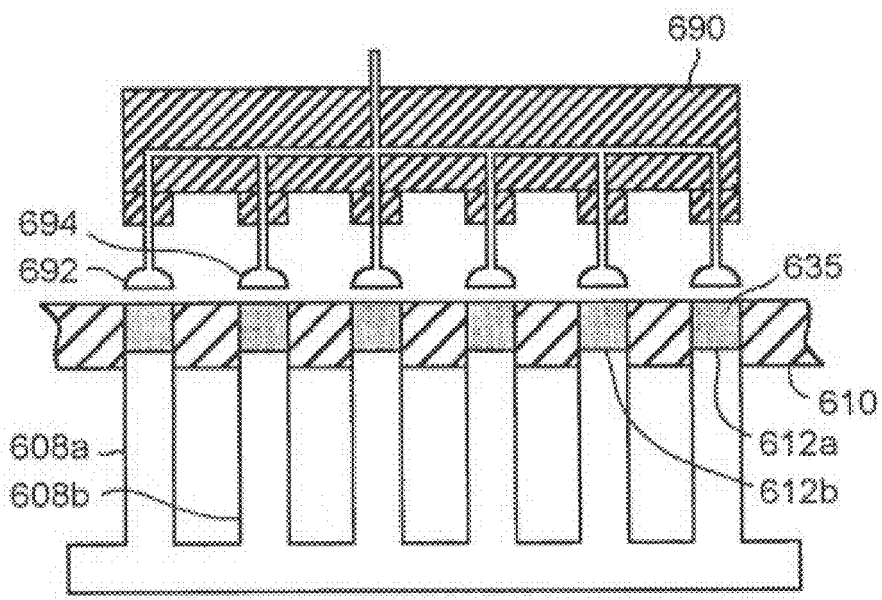
FIGS. 7a and 7b show an alternative transfer stage subsequent to the subsequent stage of FIG. 5.
Figure 7B:
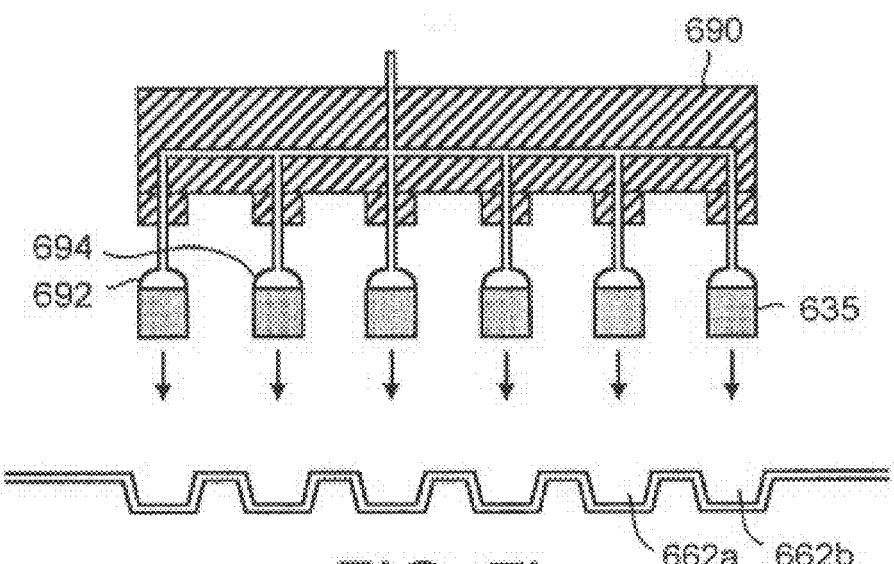

FIGS. 7a and 7b show an alternative transfer stage subsequent to FIG. 5 in which the tablets 635 are transferred by a vacuum head 690 into the container. The blanking pins 680a, 680b are raised within the perforations 612a, 612b to position the tablets 635 at the top of the perforations 612a, 612b. The vacuum head 690 comprising a series of vacuum cups 692, 694 is moved into position so that each vacuum cup 692, 694 is brought into registration with a perforation 612a, 612b. The vacuum cups 692, 694 then pick up the tablets 635 and the vacuum head 690 is lifted and moved away from the perforated plate 610 and brought into alignment with the blisters 662a, 662b of a blister pack, or into alignment with another suitable container. The tablets 635 are then transferred from the vacuum cups 692, 694 into the blister pack.

Figure 8A:
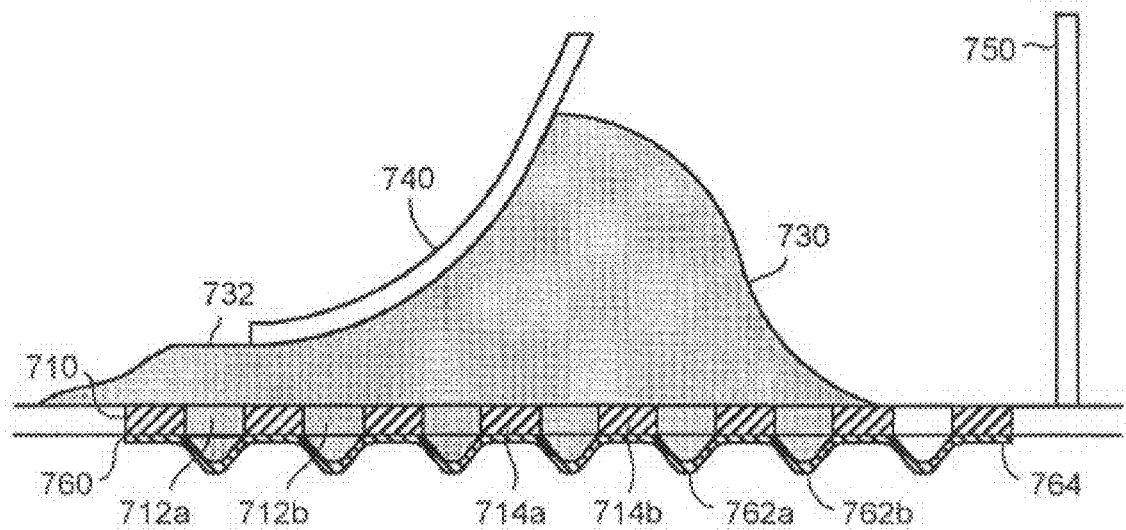
FIG. 8a shows the first stage in an alternative filling method in accord with the present invention.

FIG. 8a shows the first stage in an alternative filling method herein. A perforated plate 710 is positioned so that the blister pockets 762a, 762b of a blister strip 760 are in registration with the perforations 712a, 712b in the plate 710. The solid areas 714a, 714b of the perforated plate 710 mask the mask the surface surrounding the pockets 764 of the blister strip 760. On the opposite side of the perforated plate 710 to the blister strip 760 is a reservoir of powder 730. The powder 730 is made up of a medicament and a suitable excipient. The powder 730 is then directed into the perforations 712a, 712b (as shown in FIGS. 1a, 1b and 1c) by the action of a leveller blade 740. The leveller blade 740 shown here is curved, however a straight or articulated blade may be substituted to direct the powder into the perforations. Multiple blades (not shown) may be used to optimise the filling of the closed-off perforations 712a, 712b. The leveller blade 740 moves across the powder reservoir on a linear path 730, moving the excess powder 732 along the length of the perforated plate 710 and leaving a thin layer of powder 732 still in contact with the perforated plate 710. A wiper 750, typically a blade composed of stainless steel, follows the leveller blade 740 and moves along the powder reservoir 730 in close proximity to the surface of the perforated plate 710, removing excess powder 732 from the perforated plate surface 710.

Figure 8B:
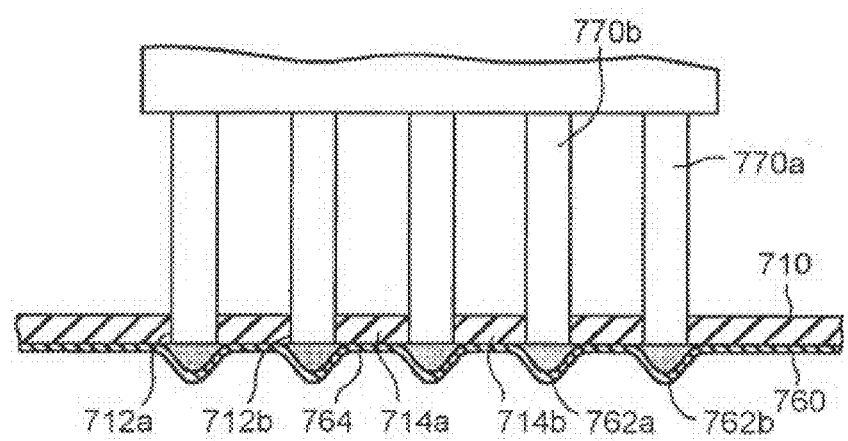

FIG. 8b shows an optional subsequent stage in which transfer and compaction pins 770a, 770b are inserted through the perforated plate 710 urging the powder 730 through into the underlying blister pockets 762a, 762b and compacting the powder 730. The pins 770a, 770b are raised and the blister strip 760 moves ready for the next section to be filled with powder 730 by the action of the leveller blade 740.

FIG. 9 shows an alternative filling method. A perforated plate 810 forms the rim of a drum 815. The powder 830 is contained within the drum 815. A blister strip 860 is positioned so that the blister pockets 862a, 862b are in registration with the perforations 812a, 812b in the plate 810. The solid areas 814a, 814b of the perforated plate 810 mask the mask the surface surrounding the pockets 864 of the blister strip 860. The blister strip 860 is fed onto and away from the drum 815 by tension alignment rollers 880, 882. A sealing station 890 is positioned so that a top foil 895 can be sealed to the blister strip 860 after it has left the drum 815.

The blister strip is fed onto the drum by tension alignment rollers 880 which align the blister strip 860 so that the blister pockets 862a, 862b are in registration with the perforations 812a, 812b in the plate 810. The powder 830 is directed into the closed-off perforations 812a, 812b and into the blister pockets 862a, 862b by gravity during rotation of the drum 815. A leveller blade (not shown) may also be used to direct the powder into the perforations 812a, 812b and a wiper (also not shown) may sometimes be used to remove excess material from the perforated plate surface 810. A stripper plate 885 removes the blister strip 860 from the drum 815 and the strip 860 is passed over another set of tension alignment rollers 882. A top foil 895 is passed over a roller at a sealing station 890 and the top foil 895 is sealed to the filled blister strip 860.

The blister strip may be sealed by applying a lid sheet and providing sealing means so that the powder is contained in a medicament container defined by the pocket and elongate strip. Suitable methods of sealing the medicament carrier include the use of adhesives, staples or stamps and welding methods selected from hot metal welding, radio frequency welding and ultrasonic welding. Such sealing techniques may be used to form a suitable seal around the periphery of the medicament pocket which is capable of being peeled away by the patient or by a suitable trigger release mechanism in a controlled manner when in use.

The invention is suitable for filling blister packs, or other suitable containers, with powdered medicament or tablets, particularly for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines, zanamivir and pentamidine; antihistamines, e.g., methapyrilene; anti-inflammatories, e.g., beclomethasone dipropionate, fluticasone propionate, flunisolide, budesonide, rofleponide, mometasone furoate, ciclesonide or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol or 4-hydroxy-7-[2-[[2-[[3-(2-phenylethoxy)propyl]sulfonyl]ethyl]amino]ethyl-2(3H)-benzothiazolone; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferred medicaments are selected from albuterol, salmeterol, ipratropium bromide, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate). A particularly preferred combination comprises salmeterol xinafoate salt and fluticasone propionate.

It may be appreciated that any of the parts of the filling apparatus which contact the powder may be coated with materials such as fluoropolymer materials which reduce the tendency of medicament to adhere thereto. Suitable fluoropolymers include polytetrafluoroethylene (PTFE) and fluoroethylene propylene (FEP). Any movable parts may also have coatings applied thereto which enhance their desired movement characteristics. Frictional coatings may therefore be applied to enhance frictional contact and lubricants used to reduce frictional contact as necessary.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims or may include, by way of example and without limitation, one or more of the following claims:

We claim:

1. Apparatus for loading a defined quantity of a powdered medicament formulation into a container for use in an inhalation device, comprising:
    a perforated plate which has a first side on which powdered medicament formulation is, in use, disposed, a second side and a perforation having a first opening in the first side and a second opening in the second side,
    a closing member located at the second side of the perforated plate for closing the perforation at the second opening to enable filling of the perforation with a defined quantity of powdered medicament formulation through the first opening,
    at least one leveler non-contactingly spaced from the first side of the perforated plate for directing powdered medicament formulation located on the first side into the perforation through the first opening, the at least one leveler having a leveling face oriented at an acute angle to the first side of the perforated plate,
    a wiper located at the first side of the perforated plate for wiping away powdered medicament formulation overlying the first opening of the perforation, and
    a compacting pin insertable into the perforation through the first opening to compact and eject powdered medicament formulation in the perforation;
    wherein the apparatus is configured and arranged to provide for relative movement of the perforated plate, the closing member, the at least one leveler, the wiper and the compacting pin to successively effect:
    i) a filling mode, in which the closing member closes the second opening of the perforation and relative movement is provided between the at least one leveler and the wiper, on the one hand, and the perforated plate, on the other hand, which results in successive movement of the at least one leveler and the wiper over the first opening of the perforation to fill the closed perforation with a defined quantity of a powdered medicament formulation which is located on the first side of the perforated plate on the relative path of movement of the at least one leveler and the wiper,
    ii) a compacting mode, in which the compacting pin is inserted through the first opening of the perforation so as to compact the defined quantity of powdered medicament formulation in the closed perforation from the filling mode, and
    iii) a loading mode, in which the closing member opens the second opening and the compacting pin ejects the compacted powdered medicament formulation from the compacting mode through the second opening for loading a container for an inhalation device in registration with the second opening.

2. Apparatus according to claim 1, wherein the closing member is a blanking plate.

3. Apparatus according to claim 1, wherein the closing member is a blanking pin insertable into the perforation through the second opening.

4. Apparatus according to claim 3, wherein the blanking pin is movable within the perforation to adjust the volume of the closed-off perforation.

5. Apparatus according to claim 1, wherein the acute angle is between 1 and 60°.

6. Apparatus according to claim 1, wherein the acute angle is between 5° and 25°.

7. Apparatus according to 1, wherein the leveling face presents multiple acute angles to the first side of the perforated plate.

8. Apparatus according to claim 7, wherein the leveling face is curved in form.

9. Apparatus according to claim 7, wherein the leveling face is articulated.

10. Apparatus according to claim 1, wherein the leveling face has a flat tail section.

11. Apparatus according to claim 1, wherein there are plural levelers arranged to move in succession along the path.

12. Apparatus according to claim 11 wherein the levelers are arranged to provide a leading leveler and at least one trailing leveler and wherein the leading leveler is spaced from the first side of the perforated plate by a distance which is not less than that of the least one trailing leveler.

13. Apparatus according to claim 1, wherein the perforated plate has plural said perforations and each perforation is associated with a compacting pin.

14. Apparatus according to claim 3, wherein the perforated plate has plural said perforations and each perforation is associated with a blanking pin.

15. Apparatus according to claim 1, wherein the perforated plate is static and the at least one leveler and the wiper are movable.

* * * * *